Figure 1:
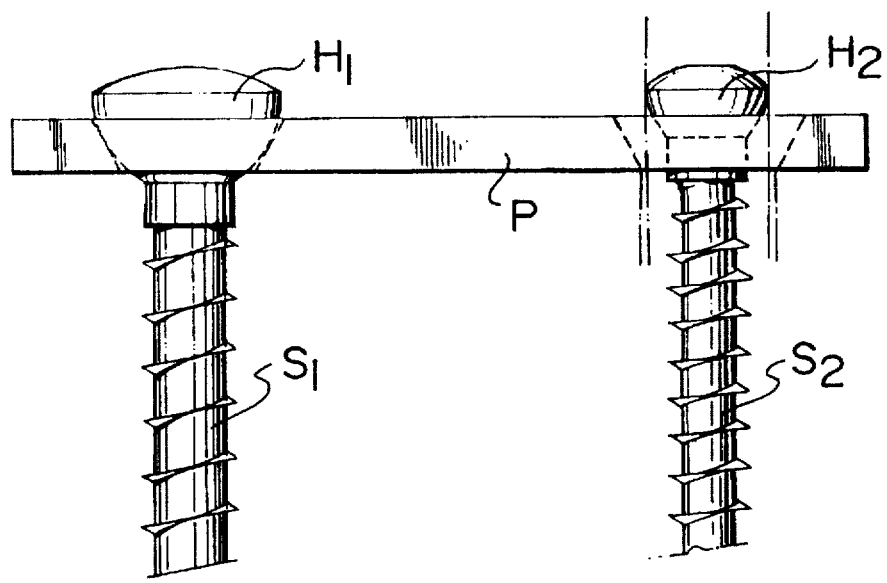

United States Patent [19]
Runciman et al.

[11] Patent Number: 5,797,912
[45] Date of Patent: Aug. 25, 1998

[54] WASHER FOR USE WITH A BONE SCREW

[75] Inventors: John Runciman, Renfrew, Canada; Samuel G. Agnew, Little Rock, Ark.; Ross Kenneth Leighton, Halifax, Canada

[73] Assignee: Terray Corporation, Ontario, Canada

[21] Appl. No.: 916,741

[22] Filed: Aug. 19, 1997

Related U.S. Application Data

[63] Continuation of Ser. No. 558,431, Nov. 16, 1995, abandoned.

[30] Foreign Application Priority Data

Sep. 22, 1995 [CA] Canada ................................ 2158890

[51] Int. Cl.$^6$ ........................................... A61B 17/80
[52] U.S. Cl. ........................................ 606/69; 606/73
[58] Field of Search ........................... 606/69, 71, 72, 606/73

[56] References Cited

U.S. PATENT DOCUMENTS

| | | | |
|---|---|---|---|
| 1,025,008 | 4/1912 | Miner | 606/71 |
| 1,077,045 | 10/1913 | Dodds | 411/380 |
| 1,264,570 | 4/1918 | Stafford | 411/379 |
| 1,333,372 | 3/1920 | Barrow | 411/379 |
| 1,352,285 | 9/1920 | Landgraf | 29/890.051 |
| 1,385,780 | 7/1921 | Dodds | 411/380 |
| 1,409,157 | 3/1922 | Dodds | 411/379 |
| 3,534,731 | 10/1970 | Muller | 606/105 |
| 3,596,656 | 8/1971 | Kaute | 606/65 |
| 3,695,259 | 10/1972 | Yost | 606/69 |
| 4,338,926 | 7/1982 | Kummer et al. | 606/70 |
| 4,388,921 | 6/1983 | Sutter et al. | 606/71 |
| 4,484,570 | 11/1984 | Sutter et al. | 606/72 |
| 4,662,887 | 5/1987 | Turner et al. | 623/16 |
| 4,805,602 | 2/1989 | Puno et al. | 606/61 |
| 4,805,612 | 2/1989 | Jensen | 128/204.21 |
| 4,943,292 | 7/1990 | Foux | 606/70 |
| 4,988,351 | 1/1991 | Paulos et al. | 606/72 |
| 5,041,113 | 8/1991 | Biedermann | 606/61 |
| 5,053,036 | 10/1991 | Perren et al. | 606/69 |
| 5,057,111 | 10/1991 | Park | 606/69 |
| 5,108,399 | 4/1992 | Eitenmuller et al. | 606/77 |
| 5,127,914 | 7/1992 | Calderale | 606/65 |
| 5,129,899 | 7/1992 | Small et al. | 606/61 |
| 5,147,363 | 9/1992 | Harle | 606/73 |
| 5,151,103 | 9/1992 | Tepic et al. | 606/69 |
| 5,209,751 | 5/1993 | Farris et al. | 606/61 |
| 5,234,431 | 8/1993 | Keller | 606/70 |
| 5,269,784 | 12/1993 | Mast | 606/69 |
| 5,344,421 | 9/1994 | Crook | 606/61 |

OTHER PUBLICATIONS

"Other Implants", catalog extract, Zimmer, Inc., 1987, p. C57 and back cover.

*Primary Examiner*—Michael Powell Buiz
*Assistant Examiner*—David O. Reip
*Attorney, Agent, or Firm*—Pearne, Gordon, McCoy & Granger LLP

[57] ABSTRACT

A washer for use with a bone screw has a head of a first diameter. The washer has a generally hemispherical recess dimensioned to fit the head of such bone screw, and an exterior shape closely approximating the shape of a head of a bone screw and having a second diameter that is larger than the first diameter.

6 Claims, 2 Drawing Sheets

WASHER FOR USE WITH A BONE SCREW

This is a continuation of application Ser. No. 08/558,431, filed Nov. 16, 1995 now abandoned.

The present invention relates to the field of medical devices. In particular, the present invention relates to a novel washer for use with a bone screw, and to the combination of a bone screw and the washer.

A bone screw is a screw designed for use by orthopaedic surgeons to assist in the setting of a fractured bone, or to attach a further device, such as a bone plate or strip to a bone surface. The world market has called for the standardization of bone screw quality, which was previously left up to individual manufacturers. The International Organization for Standardization (ISO) has now defined world standards for implant specifications and tolerances. While ISO does not dictate these standards, they are recommended and manufacturers typically choose to comply with such standards in order for there to be uniformity in the industry. Thus, bone screws are typically available in a number of standardized diameters such as 1.5 mm with a 3 mm head; 2 mm with a 4 mm head; 2.7 mm with a 5 mm head; 3.5 mm with a 6 mm head; and 4.5 and 6.5 mm, each of which has an 8 mm head. The heads of these bone plate screws, in each case, are typically substantially hemispherical, although flat head and conical head bone plate screws are also available. The advantage of the spherical head bone plate screws is that they permit the screw to be angled, if necessary, relative to the bone plate, and still make positive contact around a maximum extent of the perimeter of its head with the edge of the aperture in the bone plate. To this end the screw apertures in bone plates may be typically elongated, and may be somewhat cupped to establish positive contact with the screw head.

Sometimes, a surgeon will choose to utilize a washer between the screw head and the bone or bone plate, for substantially conventional reasons. For instance, it is known to provide a lock washer between a screw head and a bone plate. It is also known, for instance as shown in U.S. Pat. No. 5,057,111, to utilize a polymeric, generally hemispherical washer, to moderate the pressure that is exerted by a screw head on a bone during the healing process. In U.S. Pat. No. 5,269,784, a bushing having a generally hemispherical shape is described, for adapting a bone plate for use with a device for spacing the bone plate from a bone.

As noted above, bone screws are commonly available in a number of sizes. For instance, 3.5 mm screws have 6 mm heads. Medium (4.5 mm) and large (6.5 mm) screws have 8 mm heads. It will be understood therefore that some bone plates and strips are provided with apertures suitable for 6 mm heads and others with apertures for 8 mm heads, with the design of the apertures being such that the screw heads are somewhat countersunk so as not to bulge out excessively. In some instances, however, it would be desirable to utilize a smaller diameter screw to fasten a portion of a bone plate designed for larger screws that is otherwise being fastened by such larger screws. For instance, the thickness of bone available to be drilled out to set a screw may not permit a 4.5 or 6.5 screw in certain aperture locations, but these screws may be absolutely necessary in other locations. Heretofore, the available solution would be to use a flat washer with a small diameter screw, and bear the consequences of having the screw head bulge against the overlying skin or other tissues. A further consequence of using a flat washer in such a situation is that insufficient compressive force across a fracture may be the result of not having the screw head seat positively in the aperture of the bone plate.

The present invention provides a washer to adapt a smaller diameter screw to interact with a bone plate in the manner of a larger diameter screw. Moreover, the washer of the present invention permits a small diameter screw to be used instead of a large diameter screw, where an extremely shallow angle between the plate and the screw, unattainable with a larger diameter screw, is required.

An advantage of the present invention is that it provides a washer which can be used to selectively fit over a screw head to modify or increase the effective screw head size for a given diameter shaft. This invention enables available plates and screws to be more universal in use.

In a broad aspect, therefore, the present invention relates to a washer for use with a bone screw having a head of a first diameter, said washer having a generally hemispherical recess dimensioned to fit said first diameter head of said screw, and an exterior shape closely approximating the shape of a head of a bone screw and having a second diameter that is larger than said first diameter.

In another broad aspect, the present invention relates to, in combination, a bone screw having a head of a first diameter that is generally hemispherical, and a shaft; and a washer with a recess dimensioned and shaped to accommodate said head of said first diameter and an external shape closely approximating the shape of the head of the bone screw and having a second diameter that is larger than said first diameter.

The said first head diameter is generally selected from the group including 3 mm, 4 mm, 5 mm, 6 mm and 8 mm. The said second head diameter is selected generally from the group including 4 mm, 5 mm, 6 mm, 8 mm, and 10 mm. However, any suitable head diameters or shapes can be utilized, as appropriate.

Generally, the said washer is provided with a central aperture of a diameter selected from the group including 1.5 mm, 2 mm, 2.7 mm, 3.5 mm, 4.5 mm, and 6.5 mm.

Figure 2:
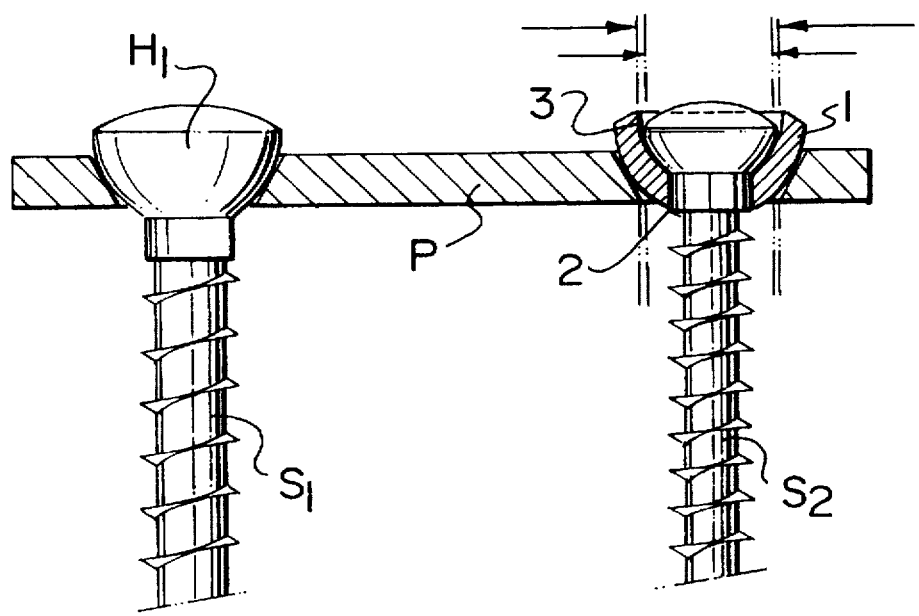
Figure 3:
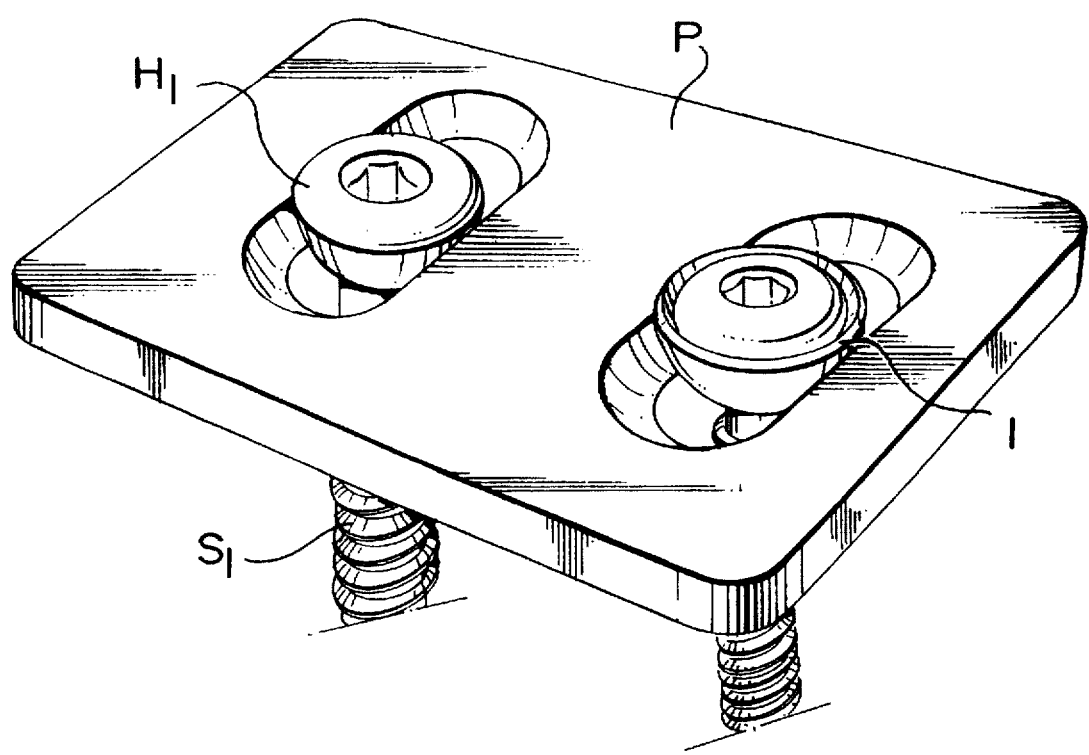

In drawings that illustrate the present invention by way of example:

FIG. 1 is a front view of a typical bone plate, with two screws in place: a large diameter screw with a large diameter head, and a small diameter screw with a small diameter head, illustrating the relative sizes of a standard 6 mm screwhead of a 3.5 mm screw, and a standard large aperture of a bone plate designed for 4.5 or 6.5 mm screws, with 8 mm heads;

FIG. 2 is a cross-sectional view through the longitudinal axes of the screws illustrated in FIG. 1, but with a washer of the present invention in place; and FIG. 3 is a perspective view, from above, of a bone plate, with a larger diameter screw, and a smaller diameter screw and washer combination of the present invention in place on the bone plate.

In the drawings, the large diameter screw is shown on the left with a threaded shaft $S_1$, and a generally hemispherical head $H_1$, which seats in an aperture in a bone plate P. The small diameter screw, on the right, has a shaft $S_2$ and a head $H_2$.

It will be noted that the diameter of the head $H_2$ of the small diameter screw is less than the width of the aperture of the bone plate, as shown in FIG. 1, and by the arrows in FIG. 2. This is because the aperture on the bone plate is dimensioned to accommodate a large diameter (8 mm) screw head, rather than a small diameter (6 mm) screw head. Accordingly, conventionally the plate shown would require the use of 4.5 mm or 6.5 mm diameter screws, each of which has a 8 mm diameter head. It is impractical to lessen the width of the aperture, because some looseness between the large diameter shaft and the aperture is desired so that if necessary, a large diameter screw can be driven at an angle to a bone plate. Moreover, it is for this reason that the screw head is hemispherically shaped. conversely, it is impractical to simply manufacture small diameter screws with larger heads instead of smaller heads for the simple reason that in some situations, a small head, occupying little space and not presenting a large bulge, is still desirable.

The present invention, therefore, provides a shell-like washer 1 having a hemispherically shaped exterior that is substantially the same in dimensions and conformation as a large diameter head.

The washer 1 of the present invention has a generally hemispherically conforming concave interior, into which fits a small diameter screw head. The aperture 2 in the centre of the washer illustrated is fractionally greater than 3.5 mm, to just accommodate a 3.5 mm diameter screw thread. Radially outwardly from the central aperture, the washer is hemispherically curved, and radially outwardly from there, exhibits a short, axially straight wall 3.

The exact shape of the washer will, however, be chosen to conform to the shape of a larger diameter screw head, since the purpose of the present invention is to provide a smaller diameter screw shaft with the head profile of a larger diameter screw. It will be noted that the present invention can also be used to increase the size of the head of a large diameter screw, from 8 mm to 10 mm, for special application. The washer of the present invention can be designed to mate with any suitable shape or size screw head in order to selectively modify or increase the effective screw head size, as desired. Any suitable plate design may be utilized in accordance with the invention with any suitable shaped screw holes which correspond to the desired mating undersurface of the corresponding bone screw heads.

The washer of the present invention is preferably fabricated of certified stainless steel, for use with bone plates and screws made of the same material. However, it is understood that any suitable materials may be utilized.

It is to be understood that the examples described above are not meant to limit the scope of the present invention. It is expected that numerous variants will be obvious to the person skilled in the field to which the present invention pertains without any departure from the spirit of the invention. The appended claims, properly construed, form the only limitation upon the scope of the invention.

We claim:

1. Apparatus for stabilizing a fracture in a bone comprising, in combination:

at least one bone plate fabricated from a surgically compatible metal, said at least one bone plate having at least two screw holes of a first diameter therethrough, from an upper to a lower surface thereof, with at least a portion of each said screw hole, at the upper surface of said at least one bone plate, having a concavely curved inner surface;

a selection of bone screws, each bone screw being fabricated from a surgically compatible metal, said selection of bone screws including at least one first screw and at least one second screw, each of said first and second screws having a shaft of a diameter selected to pass through said screw holes, with the shaft diameter of said at least one second screw being smaller then the shaft diameter of said at least one first screw, each screw having a head with an upper surface adapted to receive a screw driving instrument and a convexly curved lower surface from which said shaft projects, the head of said at least one first screw being dimensioned to fit snugly against said at least one bone plate, with the convex lower surface of said head of a said at least one first screw bearing against the concave inner surface of a said screw hole, and the head of said at least one second screw having a similar shape to the head of said at least one first screw, but being smaller than the head of said at least one first screw; and at least one washer fabricated from a surgically compatible metal, said at least one washer having a central aperture dimensioned to fit the shaft of said at least one second screw to permit said shaft of said at least one second screw to pass therethrough, said at least one washer having an upper surface that is concavely curved around said central aperture to accept the head of a said at least one second screw in a snug fit, and said at least one washer having a lower surface that is convexly curved and dimensioned to fit snugly against said at least one bone plate, with the convex lower surface of said at least one washer bearing against the concave inner surface of a said screw hole.

2. The combination claimed in claim 1, wherein said at least one second screw has a head diameter selected from the group consisting of 3 mm, 4 mm, 5 mm, 6 mm and 8 mm.

3. The combination claimed in claim 2, wherein said at least one washer has a diameter selected from the group consisting of 4 mm, 5 mm, 6 mm, 8 mm and 10 mm.

4. The combination claimed in claim 2, wherein said at least one second screw has a shaft diameter selected from the group consisting of 1.5 mm, 2 mm, 2.7 mm, 3.5 mm, 4.5 mm and 6.5 mm.

5. The combination claimed in claim 4, wherein said at least one washer has a central aperture of a diameter selected from the group consisting of 1.5 mm, 2 mm, 2.7 mm, 3.5 mm, 4.5 mm and 6.5 mm.

6. The combination claimed in claim 1, wherein the diameter of the head of said at least one second screw is smaller than the diameter of the screw holes in said at least one bone plate.

* * * * *

UNITED STATES PATENT AND TRADEMARK OFFICE
CERTIFICATE OF CORRECTION

PATENT NO. : 5,797,912
DATED : August 25, 1998
INVENTOR(S) : John Runciman, et al.

It is certified that error appears in the above-identified patent and that said Letters Patent is hereby corrected as shown below:

Col. 3, line 4, "shaped. conversely," should be --shaped. Conversely,--.

Col. 4, line 9 (claim 1), "then" should be --than--.

Signed and Sealed this

First Day of December, 1998

*Attest:*

BRUCE LEHMAN

*Attesting Officer*     *Commissioner of Patents and Trademarks*